United States Patent
Wood et al.

(10) Patent No.: US 8,357,209 B2
(45) Date of Patent: Jan. 22, 2013

(54) USE OF ALKANOLAMINES FOR THICKENING OXIDATIVE COLOURING EMULSION

(75) Inventors: Jonathan Wood, Weinheim (DE); Anja Aechtner, Mannheim (DE); Bernd Noecker, Tokyo (JP); Julia Harreus, Weinheim (DE); Fariba Ghiasi, Frankfurt (DE); Takeshi Lizaki, Frankfurt (DE)

(73) Assignee: KPSS-KAO Professional Salon Services GmbH, Darmstadt (DE)

( * ) Notice: Subject to any disclaimer, the term of this patent is extended or adjusted under 35 U.S.C. 154(b) by 0 days.

(21) Appl. No.: 13/269,302

(22) Filed: Oct. 7, 2011

(65) Prior Publication Data

US 2012/0030883 A1  Feb. 9, 2012

Related U.S. Application Data

(62) Division of application No. 12/746,991, filed as application No. PCT/EP2008/009568 on Nov. 13, 2008.

(30) Foreign Application Priority Data

Nov. 17, 2007 (EP) .................................... 07022274

(51) Int. Cl.
*A61Q 5/10* (2006.01)

(52) U.S. Cl. ............. 8/405; 8/435; 8/526; 8/528; 8/597; 8/604

(58) Field of Classification Search .............. 8/405, 435, 8/526, 528, 597, 604
See application file for complete search history.

(56) References Cited

U.S. PATENT DOCUMENTS

| 2,769,748 A | 11/1956 | Eckardt |
| 3,807,973 A | 4/1974 | Kimura et al. |
| 5,954,871 A | 9/1999 | Nicolas-Morgantini |
| 2003/0005526 A1* | 1/2003 | Casperson et al. ................ 8/405 |
| 2006/0128883 A1 | 6/2006 | Garrison |

FOREIGN PATENT DOCUMENTS

GB  2143809 A  2/1985

OTHER PUBLICATIONS

International Search Report of the International Search Authority mailed Feb. 26, 2009 issued by the European Patent Office.

\* cited by examiner

*Primary Examiner* — Eisa Elhilo
(74) *Attorney, Agent, or Firm* — Norris McLaughlin & Marcus PA

(57) ABSTRACT

The present invention relates to the use of alkanolamines for thickening oxidative coloring compositions. More particularly, the present invention relates to the use of alkanolamines for thickening ready to use oxidative coloring composition based on mixing two compositions wherein one comprises at least one oxidative dyeing precursor and the other comprises as least one oxidizing agent.

12 Claims, No Drawings

USE OF ALKANOLAMINES FOR THICKENING OXIDATIVE COLOURING EMULSION

This application is a Divisional of U.S. application Ser. No. 12/746,991 filed Jul. 15, 2010, now abandoned which is a 371 of International Patent Application PCT/EP/2008/009568, which claims priority to EP Application No. 07022274.0 filed on Nov. 16, 2007.

The present invention relates to the use of alkanolamines for thickening oxidative coloring compositions. More particularly, the present invention relates to the use of alkanolamines for thickening ready to use oxidative coloring composition based on mixing two compositions wherein one comprises at least one oxidative dyeing precursor and the other comprises as least one oxidizing agent.

Oxidative hair coloring has been practiced for many decades. It involves basically mixing two compositions, applying the mixture onto the hair and processing for a certain period of time. The successful homogeneous coloring is very much dependent on how homogeneously the coloring composition is applied onto the hair and if the coloring composition homogeneously stays on the hair surface. The latter is very much dependent on the consistency, in other word viscosity, of the coloring composition. In case of inappropriate consistency, low viscosity, coloring composition drips off from the hair which results in inhomogeneous colors.

An oxidative coloring composition is prepared by mixing two compositions, one of them comprises at least one oxidative dye precursor and has an alkaline pH and the other comprises at least one oxidizing agent and has an acidic pH. The consistency of the mix is not predictable beforehand since the two compositions mixed have different consistencies. It is often observed that the mixture thus obtained has much lower consistency than actually desired which raises difficulties in application onto the hair and furthermore, as mentioned above, results in unsatisfactory colorations, especially in terms of homogeneous coloring.

Furthermore, difficulties have been observed in bringing compositions, especially emulsion compositions, to the appropriate consistency values by using conventional technologies.

The present invention starts form the above mentioned problems and aims at providing a solution.

The present inventors have firstly and surprisingly observed that the use of a known alkalizing agent of the class of alkanolamines thickens oxidative coloring composition, preferably in an emulsion form, comprising at least one oxidative dye precursor.

The present inventors have secondly surprisingly found out that the use of at least one known alkalizing compound of the class of alkanolamines serves as thickening agent for oxidative dyeing composition, preferably in an emulsion form, which is the result of mixing two compositions wherein one of them comprises at least one oxidative dye precursor and preferably in an emulsion form and the other comprises at least one oxidizing agent.

Accordingly, the first subject of the present invention is the use of at least one compound according to the general formula $R_1R_2R_3N$ wherein $R_1$, $R_2$ and $R_3$ are same or different H, C1-C6 alkyl, C1-C6 monohydroxyalkyl or C2-C6 polyhydroxyalkyl with the condition that at least one of $R_1$, $R_2$ and $R_3$ is a mono or polyhydroxyalkyl for thickening an oxidative coloring composition, preferably an emulsion, comprising at least one oxidative dye precursor, optionally at least one coupling agent and optionally at least one direct dye.

Further object of the present invention is the use of at least one compound according to general formula $R_1R_2R_3N$ wherein $R_1$, $R_2$ and $R_3$ are same or different H, C1-C6 alkyl, C1-C6 monohydroxyalkyl or C2-C6 polyhydroxyalkyl with the condition that at least one of $R_1$, $R_2$ and $R_3$ is a mono or polyhydroxyalkyl for thickening an oxidative coloring composition, preferably an emulsion, resulted in mixing of two compositions A and B wherein A is preferably an emulsion and comprises at least one oxidative dye precursor, optionally at least one coupling agent and optionally at least one direct dye, and B comprises at least one oxidizing agent.

In the preferred embodiment of the present invention, at least one alkanolamine is selected from compounds according to the above general formula wherein $R_1$, $R_2$ and $R_3$ are same or different H, C1-C4 alkyl, C1-C4 monohydroxyalkyl or C2-C4 polyhydroxyalkyl with the condition that at least one of $R_1$, $R_2$ and $R_3$ is a mono or polyhydroxyalkyl.

According to the most preferred embodiment of the present invention at least one alkanolamine is selected from compounds according to the above general formula wherein $R_1$, $R_2$ and $R_3$ are same or different H, C2-C4 alkyl, C2-C4 monohydroxyalkyl or C2-C4 polyhydroxyalkyl with the condition that at least one of $R_1$, $R_2$ and $R_3$ is a mono or polyhydroxyalkyl.

Since alkanolamine compounds are alkaline compounds it is (or they are, if more than one alkanolamine is present) certainly contained in the alkaline composition which is the one comprising at least one oxidative dye precursor, optionally at least one coupling agent and optionally at least one direct dye and preferably is an emulsion.

Suitable alkanolamines according to the general formula of above are monoethanolamine, diethanolamine, triethanolamine, monoethanol methylamine, monoethanoldimethylamine, di-ethanol/methylamine, monoethanolethylamine, monoethanoldiethylamine, diethanolethylamine, monoethanolpropylamine, monoethanoldipropylamine, diethanolpropylamine, monoethanolbutylamine and diethanolbutylamine.

Preferred are monoethanolamine, diethanolamine and triethanolamine. The most preferred is monoethanolamine.

Within the meaning of the present invention it should also be understood that oxidative dyeing compositions and/or ready to use oxidative dyeing compositions can comprise more than one alkanolamine such as a mixture of two or three alkanolamines.

The concentration of at least one alkanolamine in the compositions varies between 1 and 35%, preferably 1 and 30, more preferably 2.5 and 25 and most preferably 2.5 to 20% by weight calculated to the total composition prior to mixing with the oxidizing agent.

The composition comprising at least one oxidative dye precursor, optionally at least one coupling agent and optionally at least one direct dye is preferably an emulsion and, therefore, preferably comprises one or more fatty alcohol of the general formula $R_4$—OH wherein $R_4$ is a linear or branched, saturated or unsaturated alkyl chain with 12 to 22 C atoms and at least one emulsifier selected from anionic, non-ionic, cationic and amphoteric surfactants.

Suitable fatty alcohols are myristyl alcohol, cetyl alcohol, stearyl alcohol and behenyl alcohol and their mixtures. Most preferred is the mixture of cetyl and stearyl alcohol also known as cetearyl alcohol.

The concentration of one or more fatty alcohols is in the range of 1 to 25%, preferably 2.5 to 20%, more preferably 5 to 15% and most preferably 5 to 10% by weight calculated to total composition prior to mixing with oxidizing agent.

The composition of the present invention comprises at least one emulsifier selected from anionic, non-ionic, cationic and amphoteric surfactants. Preferred emulsifying surfactants are anionic, non-ionic and cationic ones and especially preferred are the mixture of anionic and non-ionic surfactants and mixture of cationic non-ionic surfactants at any ratio. Preferred mixing ratio for the anionic—non-ionic emulsifying surfactant mixture and cationic—non-ionic emulsifying surfactant mixture is in the range of 5:1 to 1:5, more preferably 3:1 to 1:3 and especially 1:1, by weight. It should be noted that incompatibilities can arise when anionic and cationic surfactants are used as the mixture emulsifier which should be taken into account when selecting such a combination.

In principal any anionic surfactant is suitable within the meaning of the present invention. Nonlimiting examples are anionic surfactants of the sulfate, sulfonate, carboxylate and alkyl phosphate type, especially, of course, those customarily used as emulsifiers, for example, the known $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolamides, and the alkali salts thereof, as well as the salts of long-chain mono- and dialkyl phosphates and their salts.

Further suitable surfactants of the carboxylate type are alkyl polyether carboxylic acids and the salts thereof of the formula $$R_5-(C_2H_4O)_n-O-CH_2COOX,$$

wherein $R_5$ is a $C_8$-$C_{20}$-alkyl group, preferably a $C_{12}$-$C_{14}$-alkyl group, n is a number from 1 to 20, preferably 2 to 17, and X is H or preferably a cation of the group sodium, potassium, magnesium and ammonium, which can optionally be hydroxyalkyl-substituted, as well as alkyl amido polyether carboxylic acids of the general formula

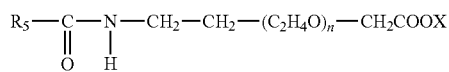

wherein $R_5$ and X have the above meanings, and n is in particular a number from 1 to 10, preferably 2.5 to 5.

Among the anionic surfactants most preferred are alkyl sulfates and/or alkyl ether sulfates and among them sodium lauryl or laureth sulfates and their mixtures are most preferred.

Suitable non-ionic surfactants are alkyl polyglucosides of the general formula $$R_6-O-(R_7O)_n O-Z_x$$

wherein $R_6$ is an alkyl group with 8 to 18 carbon atoms, $R_7$ is an ethylene or propylene group, Z is a saccharide group with 5 to 6 carbon atoms, n is a number from 0 to 10 and x is a number between 1 and 5. Examples are decyl polyglucoside and cocoyl polyglucoside, both being commercially available.

Further nonionic surfactant components are, for example, long-chain fatty acid mono- and dialkanolamides, such as coco fatty acid monoethanolamide and myristic fatty acid monoethanolamide.

Further additionally useful nonionic surfactants are, for example, the various sorbitan esters, such as polyethylene glycol sorbitan stearic acid ester, fatty acid polyglycol esters or poly-condensates of ethyleneoxide and propyleneoxide, as they are on the market, for example, under the trade name "Pluronics$^R$".

Further nonionic surfactants as emulsifiers useful in the compositions according to invention are $C_{10}$-$C_{22}$-fatty alcohol ethoxylates. Especially suited are $C_{10}$-$C_{22}$-fatty alcohol ethers, the alkyl polyglycol ethers known by the generic terms "Laureth", "Myristeth", "Oleth", "Ceteth", "Deceth", "Steareth" and "Ceteareth" according to the CTFA nomenclature, including addition of the number of ethylene oxide molecules, e.g., "Laureth-16":

The average degree of ethoxylation thereby ranges between about 2.5 and about 25, preferably about 10 and about 20.

Among the non-ionic surfactants mentioned above fatty alcohol ethoxylates and fatty acid alkanolamides and their mixtures at any weight ratio are the most preferred ones.

As a rule any mono alkyl quaternary ammonium surfactants is suitable for the compositions of the present invention as cationic emulsifying surfactant. With the term mono alkyl it is meant that quaternary ammonium surfactant includes only 1 alkyl chain which has more than 8 C atoms. The term does not exclude that the quaternary ammonium surfactant includes further short alkyl chains, $C_1$ to $C_4$, present in the molecule.

Preferably at least one mono alkyl quaternary ammonium surfactant is selected from the compounds with the general formula

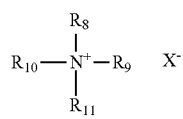

where $R_8$ is saturated or unsaturated, branched or non-branched alkyl chain with 8-22 C atoms or $$R_{12}CONH(CH_2)_n$$

where $R_{12}$ is saturated or unsaturated, branched or non-branched alkyl chain with 7-21 C atoms and n has typical value of 0-4 or $$R_{12}COO(CH_2)_n$$

where $R_{12}$ is saturated or unsaturated, branched or non-branched alkyl chain with 7-21 C atoms and n has typical value of 0-4, and $R_9$, $R_{10}$ and $R_{11}$ are independent from each other lower alkyl chain with 1 to 4 carbon atoms, hydroxyl alky chain with 1 to 4 C atoms, or ethoxy or propoxy group with number of ethoxy or propoxy groups varying in the range of 1 to 4, and X is chloride, bromide or methosulfate.

Suitable cationic surfactants and or conditioning agents are, for example, long-chain quaternary ammonium compounds which can be used alone or in admixture with one another, such as cetyl trimethyl ammonium chloride, myristoyl trimethyl ammonium chloride, behentrimonium chloride, trimethyl cetyl ammonium bromide, stearyl trimethyl ammonium chloride, stear trimonium chloride, stearamidopropyltrimethylammonium chloride, stearamidopropyl trimonuim chloride. Surfactants are included into the composition comprising at least one oxidation dye precursor, optionally at least one coupler and optionally at least one direct dye at a total concentration of 0.5 to 20%, preferably 1 to 15% and most preferably 2-10%, and most preferably 2 to 7.5% by weight, calculated to the total composition prior to mixing with the oxidizing agent.

Oxidative dyeing compositions comprise at least one oxidative dye precursor, also called developer. Suitable oxidative dyestuffs precursors are tetraaminopyrimidines, in particular 2,4,5,6-tetraminopyrimidine and the lower alkyl derivatives thereof; suitable triaminohydroxypyrimidines are, for example 4-hydroxy-2,5,6-triaminopyrimidine, 2-hydroxy-4,5,6-triaminopyrimidine and 5-hydroxy-2,4,6-triaminopyrimidine; suitable mono- and diamino dihydroxypyrimidines are, for example, 2,6-dihydroxy-4,5-diaminopyrimidine, 2,4-diamino-6-hydroxy-pyrimidine or 4,6-dihydroxy-2,5-diaminopyrimidine or the water-soluble salts thereof, aminophenol derivatives such as 4-aminophenol, 4-amino-3-methylphenol, 2-chloro-4-aminophenol, 2,6-dichloro-4-aminophenol, 2,4-diamino-phenol, 2,6-dibromo-4-aminophenol and/or 2-aminophenol and water-soluble salts thereof, furthermore, phenylenedimanine derivatives such as 2,5-diamino-toluene, 2-n-propyl or 2-ethyl-p-phenylene-diamine, 2,6-dimethyl-p-phenylenediamine, 2-(2,5-diaminophenyl) ethanol, 1-amino-4-bis-(2'-hydroxy-ethyl)aminobenzene, 2-(2-hydroxyethyl amino)-5-aminotoluene, 4,4'-diaminodiphenylamine, 4-aminodiphenylamine, 2-amino-5-N,N-diethyl aminotoluene, 4-amino-N-ethyl-N-isopropyl aniline, 2-chloro-p-phenylenediamine, 1-β-hydroxyethyl-2,5-diamino-4-chlorobenzene, 1-β-hydroxyethyl-2,5-diamino-4-methyl benzene, 2-methoxy-p-phenylenediamine, N,N-diethyl-p-phenylenediamine, 1-amino-4-β-methoxyethyl aminobenzene, 1-dimethyl-amino-4-aminobenzene, 1-hydroxy-2,5-diamino-4-methyl benzene, 1-hydroxymethyl-2,5-diaminobenzene, 1,3-dimethyl-2,5-diaminobenzene, 1,4-diamino isopropyl benzene and/or 1-amino-4-β-hydroxypropyl aminobenzene or the water-soluble salts thereof, pyrazole derivatives such as 1-hydroxyethyl-4,5-diaminopyrazole, 3,4-diamino-5-hydroxypyrazole, 3,5-diaminopyrazole, 3,5-diamino pyrazol-1-carboxamide, 3-amino-5-hydroxypyrazole, 1-phenyl-2-methylpyrazole, 1-phenyl-3-methylpyrazole-5-one, 3,5-dimethylpyrazole, 3,5-dimethylpyrazole-1-methanol, 1-methyl-4,5-diaminopyrazole, 1-methylethyl-4,5-diaminopyrazole, 1-phenylmethyl-4,5-diaminopyrazole, 1-methyl-4,5-diaminopyrazole, 1-(4-methylphenyl)methyl-4,5-diaminopyrazole, 1-methyl-3-phenyl-4,5-diaminopyrazole and the water-soluble salts. The use of the above mentioned oxidative dye precursors as mixture is also customary in hair coloring area.

The total concentration of the oxidation dyestuff precursors and/or their water soluble salts customarily ranges between about 0.05% and 5%, preferably 0.1% and 4%, in particular 0.1% to 3% by weight, calculated to the total hair dyeing composition prior to mixing with oxidizing agent, whereby these figures are always related to the proportion of free base.

The composition according to the invention optionally comprises at least one coupling substance, which can be selected from resorcinol, 2-methyl resorcinol, 4-chlororesorcinol, 2-amino-4-chlorophenol, 5-amino-4-methoxy-2-methylphenol, 3-amino-phenol, 1-methyl-2-hydroxy-4-aminobenzene, 3-N,N-dimethyl aminophenol, 2,6-dihydroxy-3,5-dimethoxypyridine, 5-amino-3-methylphenol, 6-amino-3-methylphenol, 3-amino-2-methylamino-6-methoxypyridine, 2-amino-3-hydroxy-pyridine, 2-dimethyl-amino-5-aminopyridine, 2,6-diaminopyridine, 1,3-diamino-benzene, 1-amino-3-(2'-hy-droxyethylamino)benzene, 1-amino-3-[bis(2'-hydroxy-ethyl)amino]benzene, α-naphthol, 4,6-dichlororesorcinol, 1,3-diamino-toluene, 1-hydroxy naphthalene, 4-hydroxy-1,2-methylenedioxy benzene, 1,5-dihydroxy naphthalene, 1,6-dihydroxy naphthalene, 1,7-dihydroxy naphthalene, 2,7-dihydroxy naphthalene, 1-hydroxy-2-methyl naphthalene, 4-hydroxy-1,2-methyldioxy benzene, 2,4-diamino-3-chlorophenol, 5-amino-2-methoxyphenol and/or 1-methoxy-2-amino-4-(2'-hydroxyethyl amino)benzene or the water-soluble salts thereof. However, this shall not exclude the addition of further developing and coupling substances. In the preferred embodiment of the present invention composition comprise additionally at least one coupling agent.

The weight proportion of the named developing substances to the coupling substances ranges between about 1:8 to 8:1, preferably about 1:5 to 5:1, in particular 1:2 to 2:1. In the hair dyeing compositions according to the invention, the coupling substance(s) as reaction partners of the developing substance (s) are present in approximately the same molecular proportions as the developing substances, i.e. in amounts from 0.01% to 5.0%, preferably 0.05% to 4%, in particular 0.1% to 3% by weight, calculated to the total composition prior to mixing with oxidizing agent, whereby these figures are always related to the proportion of free base.

The composition of the present invention can comprise additionally direct dyes of neutral, cationic and anionic character. Some examples to suitable cationic dyes are Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Red 2, Basic Red 12 Basic Red 22, Basic Red 51, Basic Red 76, Basic Violet 1, Basic Violet 2, Basic Violet 3, Basic Violet 10, Basic Violet 14 and Basic Yellow 57. According to the invention, suitable cationic dyestuffs are in principal those any available on the market for cosmetic hair colouring applications. For this purpose, special reference is made to the PCT application WO 95/15144 of Ciba-Geigy AG. The content of the PCT application WO 95/15144 is by reference incorporated here.

Examples to suitable direct acting anionic dyes are Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium.

Some examples to those suitable neutral dyes (HC dyes), so called nitro dyes, are HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

Plant dyestuffs can also be used alone or in combination with synthetic direct-acting dyestuffs, for example henna (red or black), alkanna root, laccaic acid, indigo, logwood powder, madder root and rhubarb powder, etc.

According to the invention, the coloring composition comprises direct hair dyes at a total concentration of 0.01 to 5%, preferably 0.05 to 3%, more preferably 0.1 to 2% by weight calculated to total composition excluding the oxidative composition.

The hair dyeing composition comprising at least one oxidative dye precursor according to the present invention can comprise an organopolysiloxane wherein at least one silicon atom is linked to an alkylene group having a hetero-atom, in particular a nitrogen atom, with a poly-(N-acyl alkyleneimine) units of the formula

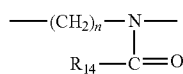

wherein n is a number from 1 to 5 and $R_{14}$ is hydrogen, a $C_1$-$C_{12}$-alkyl or cycloalkyl, aralkyl or aryl group.

Preferred organopolysiloxane polymers are those of the type disclosed in EP-A 640 643, in particular optionally quaternized aminoalkyl, in particular aminopropyl dimethyl polysiloxane/polyethyl oxazoline copolymers of the formula

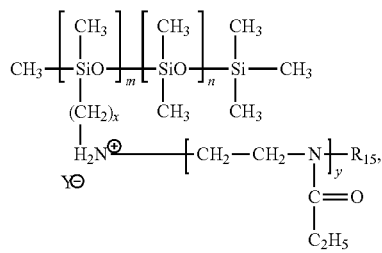

wherein m an n each are numbers from 20 to 10,000, in particular 50 to 7,000, especially 100 to 5,000, x is a number between 1 and 5, preferably 3, and y is a number from 5 to 30, $R_{15}$ is a $C_1$-$C_{12}$-alkyl or aryl group, in particular a methyl, ethyl or benzyl group, and $Y^-$ is an anion.

Especially suited are the organopolysiloxanes disclosed under the terms A-1, A-2 and A-3 on pages 12 to 13 of EP-A 640 643. The proportion of graft copolymers in the hair colouring compositions according to the invention ranges from 0.05% to 5%, preferably 0.1% to 2.5%, in particular 0.5% to 1.5% by weight, calculated to the total composition.

Another compound that may be comprised in the colouring composition comprising at least one oxidative dye precursor is a ceramide type of compounds according to the general formula

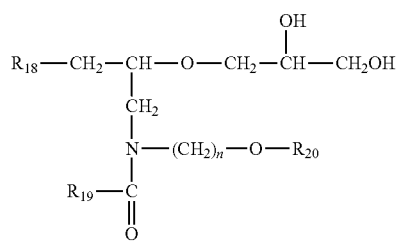

where $R_{18}$ and $R_{19}$ are independent from each other alkyl- or alkenyl group with 10 to 22 carbon atoms, $R_{20}$ is methyl, ethyl, n-propyl or isopropyl group and n is a number between 1 to 6, preferably 2 or 3. The concentration of the ceramide type of compound in colouring compositions of the present invention can be in the range of 0.01 to 2 and especially 0.01 to 1% by weight calculated to the total composition.

The compositions comprising at least one oxidative dye precursor according to the present invention can further comprise one or more ubiquinone of the formula.

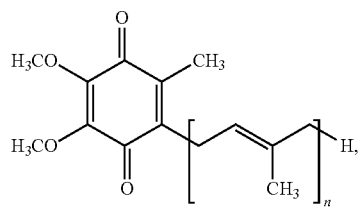

wherein n is a number from 1 to 10. The concentration of ubichinones in the compositions of the present invention can vary between 0.001% and 10% by weight, calculated to the total composition excluding the oxidizing agent.

The coloring composition of the present invention can certainly comprise compounds for accelerating (catalysts) the oxidative dyeing keratin fibres such as iodine salts i.e. potassium or sodium iodide and/or dihydroxy acetone.

Further compositions can comprise yogurt powder at a concentration of 0.01 to 5% by weight calculated to total composition prior to mixing with oxidizing agent, which is a raw material prepared by spray drying of natural yoghurt after completion of fermentation. Yogurt powder comprises the following major components:
- approximately 53.5% lactose,
- approximately 25% proteins,
- approximately 7.5% lactic acid,
- approximately 5% minerals and trace elements,
- approximately 1% vitamines, and
- approximately 2% lipids.

Compositions comprising at least one oxidative dye precursor are alkaline compositions and can comprise in addition to the alkanolamines further alkalizing agents such as ammonia.

The pH-value of the ready-to-use hair dyeing composition, i.e. after mixing with peroxide, can be between 5 and 12, preferably 6-11, more preferably 6.8 to 10.

The pH of the composition comprising at least one oxidative dye precursor is between 5 and 12, preferably 6-11, more preferably 6.8 to 10.

The preferred oxidizing agent is hydrogen peroxide, for example in a concentration of 2 to 12% by weight. However, the use of other peroxides such as urea peroxide and melamine peroxide is also possible. The oxidizing base can comprise surfactants of anionic, nonionic and zwitterionic character wherein anionic and nonionic surfactants are preferred and anionic and/or nonionic polymers for thickening purposes.

The pH of the composition comprising at least one oxidizing agent is in the range of 2 to 5, preferably 2.5 to 4 and more preferably 3 to 4.

The viscosity of the compositions comprising an oxidative dye precursor prior to mixing with an oxidizing agent is in the range of 800 to 5000 mPa·s, preferably 1000 to 4000 mPa·s measured at 25° C. with a Paar Physica Viscosimeter UDS 200 at a share rate of 100/s.

The viscosity of the ready to use compositions obtained after mixing the oxidative dye precursor comprising composition and the composition comprising at least one oxidizing agent, is in the range of 800 to 5000 mPa·s, preferably 1000 to 4000 mPa·s measured at 25° C. with a Paar Physica Viscosimeter UDS 200 at a share rate of 100/s.

The hair dyeing compositions according to the invention can comprise basic substances and additives customarily found in such compositions, such as conditioning agents, reducing agents, stabilizers for oxidizing agent, foam preventing agents etc., known as state of the art.

The following examples are to illustrate the invention without limiting it.

EXAMPLE 1

| Hair dyeing composition | |
|---|---|
| | % by weight |
| Cetearyl alcohol | 10.8 |
| Oleth-5 | 5.0 |
| Oleic acid | 2.5 |
| Stearamide MEA | 2.3 |
| Cocamide MEA | 2.3 |
| Sodium cetearyl sulfate | 1.0 |
| Propylene glycol stearate | 0.6 |
| Sodium lauryl sulfate | 0.5 |
| Sodium sulfite | 1.0 |
| Ammonia 25% | A (see Table I below) |
| Triethanolamine | B (see Table I below) |
| Toluene 2,5-diamine sulfate | 0.6 |
| 2-Methylresorcinol | 0.2 |
| Resorcinol | 0.1 |
| 2-Amino-3-hydroxypyridine | 0.05 |
| 2,5,6-Triamino-4-pyrimidinol sulfate | 0.02 |
| Water | q.s. to 100 |

The above composition was prepared with varying concentrations of ammonia and triethanolamine as given below in Table I. Viscosity values were measured at 25° C. with a Paar Physica Viscosimeter UDS 200 at a share rate of 100/s.

TABLE I

| Viscosity values of compositions | | | |
|---|---|---|---|
| Composition | % Ammonia* (A) | % Triethanolamine (B) | Viscosity (mPa · s) |
| 1 | 9.6 | 0 | 935 |
| 2 | 7.2 | 5.3 | 968 |
| 3 | 4.8 | 10.5 | 1250 |
| 4 | 2.4 | 15.8 | 1910 |
| 5 | 0 | 21.1 | 3700 |

As clear from the above results viscosity values form the composition increases with increasing content of triethanolamine.

In all compositions above the total alkalinity value of the compositions was kept constant at 2.4% as measured with an automatic titrator Mettler Toledo DL578.

Similar results were obtained when monoethanolamine was used instead of triethanolamine.

EXAMPLE 2

The above composition was prepared using monoethanolamine instead of triethanolamine. The monoethanolamine concentration is varied as shown in Table II below.

In all compositions the total alkalinity value of the compositions was kept constant at 2.4% as measured with an automatic titrator Mettler Toledo DL578.

The composition was mixed with another composition comprising an oxidizing agent, at a weight ratio of 1 to 1, of the following formula

| | |
|---|---|
| Hydrogen peroxide | 6.0 |
| Cetearyl alcohol | 1.7 |
| Sodium lauryl sulfate | 0.2 |
| Phosphoric acid | 0.3 |
| Salicylic acid | 0.01 |
| Simethicone | 0.002 |
| Water | q.s. to 100 |

The pH of the above composition was 2.5 and it had a viscosity value of 156 mPa·s.

The measured viscosity results after mixing are summarized in Table II.

TABLE II

| Viscosity of mixture of oxidizing agent and oxidative dye precursor comprising composition at a weight ratio of 1 to 1. | | | |
|---|---|---|---|
| Composition | % Ammonia* (A) | % Monoethanolamine (B) | Viscosity (mPa · s) |
| 6 | 9.6 | 0 | 960 |
| 7 | 7.2 | 2.15 | 1080 |
| 8 | 4.8 | 4.3 | 1170 |
| 9 | 2.4 | 6.45 | 1230 |
| 10 | 0 | 8.6 | 1270 |

As clear from Table II, the viscosity value of the mixture increases as the monoethanolamine concentration increases.

The invention claimed is:

1. A method for thickening oxidative hair coloring compositions comprising adding at least one compound according to the general formula $R_1R_2R_3N$ wherein $R_1$, $R_2$ and $R_3$ are same or different H, $C_1$-$C_6$ alkyl, $C_1$-$C_6$ monohydroxyalkyl or $C_2$-$C_6$ polyhydroxyalkyl with the condition that at least one of $R_1$, $R_2$ and $R_3$ is a mono or polyhydroxyalkyl, to a hair coloring composition, said coloring composition being a mixture of a first composition comprising an oxidative dye precursor and a second composition comprising at least one oxidizing agent, wherein the coloring composition is an emulsion.

2. The method according to claim 1 wherein $R_1$, $R_2$ and $R_3$ are same or different H, $C_1$-$C_4$ alkyl, $C_1$-$C_4$ monohydroxyalkyl or $C_2$-$C_4$ polyhydroxyalkyl with the condition that at least one of $R_1$, $R_2$ and $R_3$ is a mono or polyhydroxyalkyl.

3. The method according to claim 1 compound according to the general formula $R_1R_2R_3N$ is an alkanolamine.

4. The method according to claim 3 wherein the alkanolamine is selected from monoethanolamine, diethanolamine and triethanolamine.

5. The method according to claim 4 wherein the alkanolamine is monoethanolamine.

6. The method according to claim 1 wherein the concentration of alkanolamine in the coloring composition is between about 1 to 35 wt. %.

7. The method according to claim 6 wherein the concentration of alkanolamine in the coloring composition is between about 2.5 to 20 wt. %.

8. The method according to claim 1 wherein the viscosity of the coloring composition is greater than 935 mPa·s.

9. The method according to claim 8 wherein the viscosity of the coloring composition is 1250 mPa·s or greater.

10. The method according to claim 1 wherein the coloring composition comprises at least one emulsifier selected from the group consisting of anionic, non-ionic, cationic, amphoteric surfactants and mixtures thereof.

11. The method according to claim 10 wherein the coloring composition comprises a mixture of anionic and non-ionic surfactants in a mixing ratio in the range of between 3:1 to 1:3.

12. The method according to claim 10 wherein the coloring composition comprises a mixture of cationic and non-ionic surfactants in a mixing ratio in the range of between 3:1 to 1:3.

* * * * *